US012648710B2

(12) United States Patent
Govari et al.

(10) Patent No.: US 12,648,710 B2
(45) Date of Patent: Jun. 9, 2026

(54) CATHETER WITH DISTAL TILT DETECTION

(71) Applicant: Biosense Webster (Israel) Ltd., Yokneam (IL)

(72) Inventors: Assaf Govari, Haifa (IL); Andres Claudio Altmann, Haifa (IL); Shlomo Fried, Zichron Yaakov (IL)

(73) Assignee: Biosense Webster (Israel) Ltd.—CPH, Yokneam (IL)

( * ) Notice: Subject to any disclaimer, the term of this patent is extended or adjusted under 35 U.S.C. 154(b) by 406 days.

(21) Appl. No.: 18/091,347

(22) Filed: Dec. 29, 2022

(65) Prior Publication Data
US 2024/0215853 A1      Jul. 4, 2024

(51) Int. Cl.
A61B 34/20 (2016.01)
A61B 5/06 (2006.01)

(52) U.S. Cl.
CPC ...... A61B 5/062 (2013.01); A61B 2034/2051 (2016.02)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |

| | | |
|---|---|---|
| 6,172,499 B1 | 1/2001 | Ashe |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,788,967 B2 | 9/2004 | Ben-Haim et al. |
| 6,892,091 B1 | 5/2005 | Ben-Haim et al. |
| 7,536,218 B2 | 5/2009 | Govari et al. |
| 7,756,576 B2 | 7/2010 | Levin |
| 7,848,787 B2 | 12/2010 | Osadchy |
| 7,869,865 B2 | 1/2011 | Govari et al. |
| 8,437,832 B2 | 5/2013 | Govari et al. |
| 8,456,182 B2 | 6/2013 | Bar-Tal et al. |

(Continued)

OTHER PUBLICATIONS

Extended European Search Report, received for European Application No. 23219954.7, mailed on May 27, 2024, 9 pages.

*Primary Examiner* — Amal Aly Farag
(74) *Attorney, Agent, or Firm* — FBT Gibbons LLP

(57) ABSTRACT

Medical apparatus includes a probe including a distal part adapted for insertion into a body of a living subject and first and second magnetic transducers in the distal part of the probe. Control circuitry drives the first magnetic transducer to generate a first AC magnetic field at a first frequency and drives a magnetic field generator in proximity to the body to generate a second AC magnetic field within the body at a second frequency, calculates a disposition of the distal part of the probe by processing a first signal output by the second magnetic transducer at the first frequency, and calculates position coordinates of the distal part of the probe by processing a component of a second signal output by one of the first and second magnetic transducers at the second frequency while canceling from the second signal interference at the first frequency.

20 Claims, 4 Drawing Sheets

(56)          References Cited

U.S. PATENT DOCUMENTS

| | | | |
|---|---|---|---|
| 8,535,308 B2 | 9/2013 | Govari et al. | |
| 2013/0096551 A1 | 4/2013 | Govari et al. | |
| 2013/0303886 A1 | 11/2013 | Ludwin et al. | |
| 2018/0146948 A1* | 5/2018 | Chou .................... | A61B 8/466 |
| 2023/0346459 A1 | 11/2023 | Beeckler et al. | |

* cited by examiner

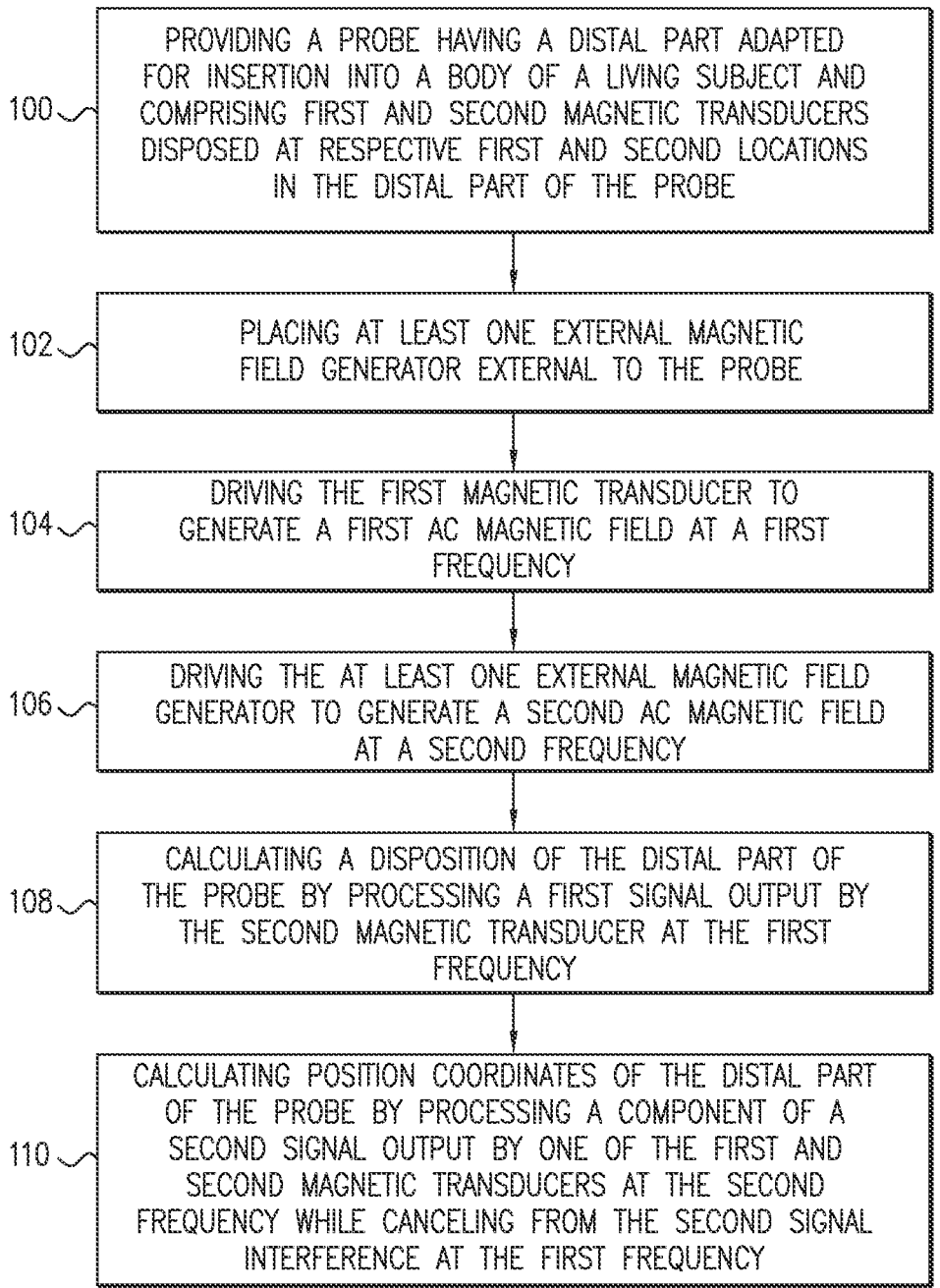

100 — PROVIDING A PROBE HAVING A DISTAL PART ADAPTED FOR INSERTION INTO A BODY OF A LIVING SUBJECT AND COMPRISING FIRST AND SECOND MAGNETIC TRANSDUCERS DISPOSED AT RESPECTIVE FIRST AND SECOND LOCATIONS IN THE DISTAL PART OF THE PROBE

102 — PLACING AT LEAST ONE EXTERNAL MAGNETIC FIELD GENERATOR EXTERNAL TO THE PROBE

104 — DRIVING THE FIRST MAGNETIC TRANSDUCER TO GENERATE A FIRST AC MAGNETIC FIELD AT A FIRST FREQUENCY

106 — DRIVING THE AT LEAST ONE EXTERNAL MAGNETIC FIELD GENERATOR TO GENERATE A SECOND AC MAGNETIC FIELD AT A SECOND FREQUENCY

108 — CALCULATING A DISPOSITION OF THE DISTAL PART OF THE PROBE BY PROCESSING A FIRST SIGNAL OUTPUT BY THE SECOND MAGNETIC TRANSDUCER AT THE FIRST FREQUENCY

110 — CALCULATING POSITION COORDINATES OF THE DISTAL PART OF THE PROBE BY PROCESSING A COMPONENT OF A SECOND SIGNAL OUTPUT BY ONE OF THE FIRST AND SECOND MAGNETIC TRANSDUCERS AT THE SECOND FREQUENCY WHILE CANCELING FROM THE SECOND SIGNAL INTERFERENCE AT THE FIRST FREQUENCY

FIG. 5

CATHETER WITH DISTAL TILT DETECTION

FIELD

The present disclosure relates to invasive medical devices, and specifically to methods and devices for sensing displacement of a distal part of a probe, such as a catheter, that is applied to the body of a patient.

BACKGROUND

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

Catheters with integrated pressure sensors for sensing tissue contact have been described in the patent literature. As one example, U.S. Pat. No. 8,535,308, whose disclosure is incorporated herein by reference, describes a medical probe, which includes an insertion tube, having a longitudinal axis and having a distal end. A distal tip is disposed at the distal end of the insertion tube and is configured to be brought into contact with a body tissue. A joint couples the distal tip to the distal end of the insertion tube. A joint sensor, contained within the probe, senses a position of the distal tip relative to the distal end of the insertion tube. The joint sensor includes first and second subassemblies, which are disposed within the probe on opposite, respective sides of the joint and each include one or more magnetic transducers.

The present disclosure will be more fully understood from the following detailed description of the examples thereof, taken together with the drawings in which:

BRIEF DESCRIPTION OF THE DRAWINGS

FIG. 5 is a flow chart that schematically illustrates a method for position sensing, in accordance with an example of the disclosure.

DETAILED DESCRIPTION

Overview

Figure 1:
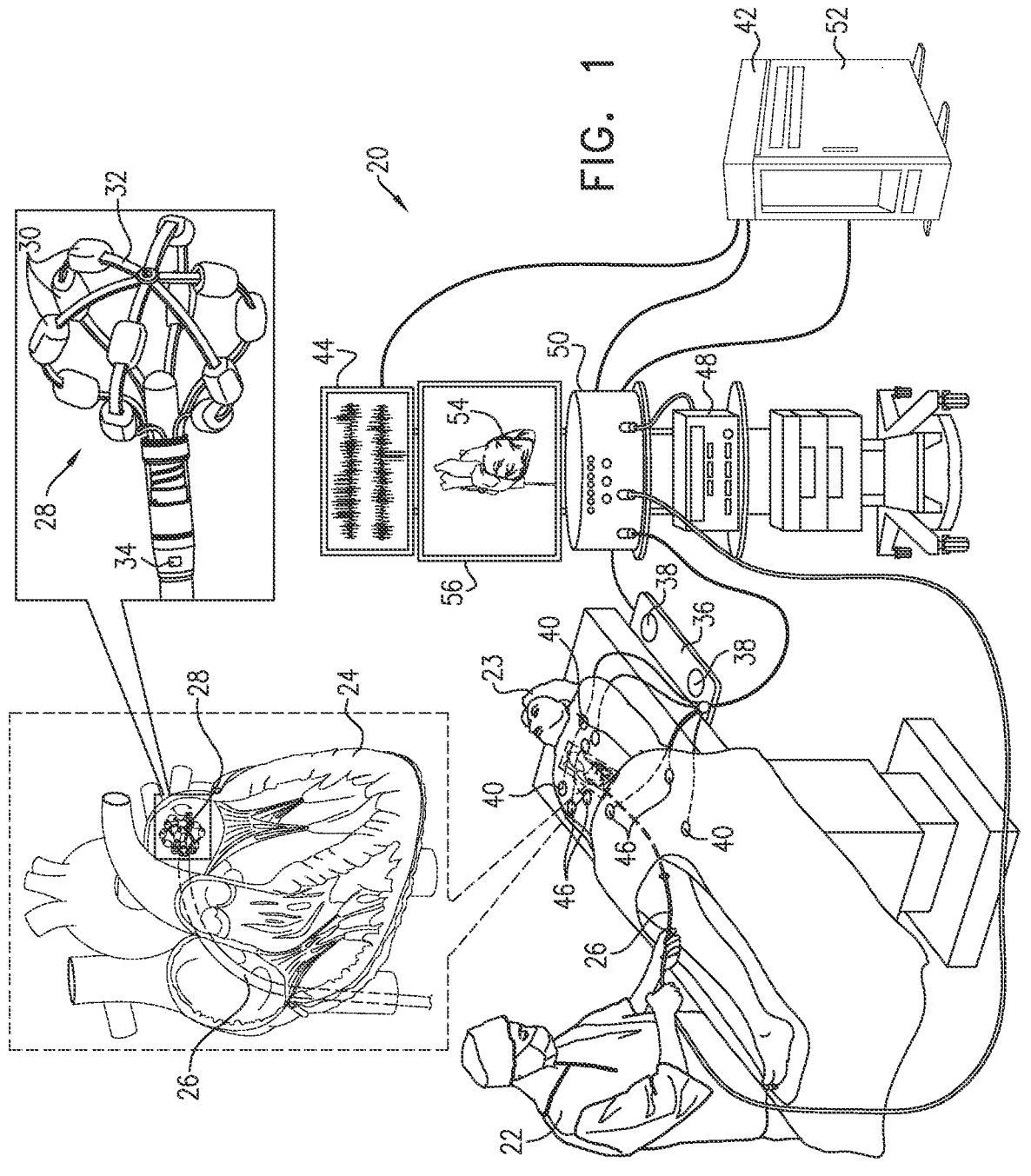
FIG. 1 is schematic pictorial illustration of a catheter-based electrophysiology mapping and ablation system, in accordance with an example of the disclosure.

Certain types of medical probes, such as catheters for insertion into chambers of the heart, contain magnetic position sensors, which are used in navigating the distal part of the probe within the patient's body. The magnetic position sensor comprises a magnetic transducer, i.e., a device that converts magnetic energy into an electrical signal, or vice versa. A magnetic field generator in proximity to the patient's body produces an alternating-current ("AC") or time-varying magnetic field within the body at a certain frequency, and the signals output by the magnetic transducer at this frequency are processed to calculate position coordinates of the distal part of the probe. Typically, the magnetic transducer comprises one or more coils; but alternatively, other types of transducers, such as Hall sensors, may be used for the present purposes.

Some probes comprise a deflectable distal assembly. For example, some cardiac catheters comprise a basket assembly at their distal end, with electrodes distributed along the spines of the basket assembly for contacting tissue within the heart. The magnetic transducer used for position sensing in these sorts of catheters is commonly located near the distal end of the catheter insertion tube, while the basket assembly extends distally away from the distal end of the insertion tube. The basket assembly may deflect transversely, relative to the axis of the insertion tube, due to force exerted by the basket assembly against the tissue. When the deflection is substantial, for example more than a few degrees, the position coordinates given by the magnetic transducer will not give an accurate reading of the locations of the electrodes on the basket assembly.

Some probes with deflectable distal assemblies include a force sensor for measuring the force exerted by the distal assembly against tissue in the body. For example, the sorts of cardiac catheters that were described above may comprise a joint between the distal end of the insertion tube and the basket assembly. The joint deforms in response to force exerted by the basket assembly against the tissue. To measure the deformation, and thus estimate the force, magnetic transducers are disposed in the catheter on opposing sides of the joint. One of the transducers, for example the transducer on the distal side of the joint, is driven to generate an AC magnetic field at a certain frequency, and the transducer (or transducers) on the other side of the joint outputs a signal at this same frequency in response to this field. Control circuitry processes the signal to calculated the deformation of the joint and thus find the magnitude and direction of the force.

In the present disclosure, at least one of the magnetic transducers in the force sensor, for example the magnetic transducer on the distal side of the joint, also serves as a position sensor, to sense the AC magnetic field that is produced by the magnetic field generator outside the patient's body. Control circuitry processes the signal component output by this magnetic transducer at the frequency of the magnetic field generator in order to calculate position coordinates of the distal part of the probe within the body. In particular, when the magnetic transducer on the distal side of the joint is used for this purpose, it will deflect together with the deflectable distal assembly and thus will give an accurate reading of the positions of the electrodes notwithstanding the deflection. For enhanced accuracy in finding the position of the distal part of the probe, the signals obtained from the magnetic transducer in the force sensor may be used together with signals provided by a magnetic transducer in the distal end of the insertion tube.

A problem still remains with this approach, however, in that in the immediate vicinity of the joint, the magnetic field transmitted by one of the magnetic transducers for the purpose of force sensing is far stronger than the magnetic field produced by the magnetic field generator outside the body. Consequently, the signal component at the frequency of the magnetic field generator will be much weaker than the signal component at the frequency of the force sensor, and an amplifier for sensing signals that the magnetic transducer in the force sensor picks up from the magnetic field generator will be saturated due to the gain of the signal transmitted for force sensing. To mitigate this problem, and thus extract a useful signal for purposes of calculating position coordinates, the control circuitry cancels interference at the frequency of the force sensor from the position signal that is obtained from the magnetic transducer in the force sensor.

In one example, since the frequency of the force sensor is known, the control circuitry measures the amplitude of the signal component at this frequency and generates an interference cancellation signal of the same amplitude but opposite phase. For precise interference cancellation, the control circuitry may desirably measure the exact frequency and phase of the signal component at the force sensor frequency and apply this measurement in generating the interference cancellation signal. This interference cancellation signal is summed with the signal that is received from the magnetic transducer in the force sensor, so that what remains following summation is the signal component at the frequency of the magnetic field generator. The control circuitry processes this remaining signal component in order to calculate the position coordinates. #

Although the examples described below and shown in the figures relate specifically to a catheter with a distal basket assembly, the principles of the present disclosure may similarly be applied, mutatis mutandis, in finding accurate position coordinates of the distal parts of other sorts of probes, and particularly probes with other sorts of distal assemblies.

System Description

FIG. 1 shows an example catheter-based electrophysiology mapping and ablation system 20. System 20 may include multiple catheters, which are percutaneously inserted by a physician 22 through the vascular system of a patient 23 into a chamber or vascular structure of a heart 24. Typically, a delivery sheath (not shown) is inserted into the left or right atrium near a desired location in heart 24. Thereafter, one or more catheters 26 are inserted through the delivery sheath so as to arrive at the desired location in heart 24. The multiple catheters may include catheters dedicated for sensing intracardiac electrogram (IEGM) signals, catheters dedicated for ablating, and/or catheters used for both sensing and ablating. The distal part of catheter 26 in the pictured example comprises a basket assembly 28. Physician 22 may manipulate catheter 26 to place basket assembly 28 in contact with the heart wall for sensing a target site in heart 24 and/or for ablating tissue at the target site.

Catheter 26 is an exemplary catheter that includes multiple electrodes 30 distributed over a plurality of spines 32 in basket assembly 28 and configured to sense IEGM signals and/or ablate myocardial tissue. Catheter 26 additionally includes one or more position sensors 34 embedded in the distal part of the catheter for tracking the position and orientation of basket assembly 28, as described further hereinbelow. For example, position sensor 34 may comprise a magnetic position sensor including three magnetic coils for sensing three-dimensional (3D) position and orientation.

Magnetic position sensors 70, 72 and 74 (shown in FIG. 3, and optionally also magnetic position sensor 34) may be operated together with a location pad 36 including multiple magnetic coils 38 (shown as coils 38a, 38b, 38c in FIG. 3) configured to generate magnetic fields in a predefined working volume containing heart 24. The position of basket assembly 28 of catheter 26 may be tracked based on magnetic fields generated by location pad 36 and sensed by magnetic position sensor 34 (which may include three orthogonal coils). Details of magnetic position sensing technology that may be applied for this purpose are described, for example, in U.S. Pat. Nos. 5,391,199; 5,443,489; 5,558,091; 6,172,499; 6,239,724; 6,332,089; 6,484,118; 6,618,612; 6,690,963; 6,788,967; and 6,892,091.

System 20 optionally includes one or more electrode patches 40 in contact with the skin of patient 23 to establish location references for location pad 36, as well as for impedance-based tracking of electrodes 30. For impedance-based tracking, electrical current is directed to electrodes 30 and sensed at electrode patches 40 so that the location of each electrode 30 can be triangulated via electrode patches 40. Details of this sort of impedance-based location tracking technology are described in U.S. Pat. Nos. 7,536,218; 7,756,576; 7,848,787; 7,869,865; and 8,456,182.

A recorder 42 records and displays electrograms 44 captured by body-surface ECG electrodes 46 and intracardiac electrograms (IEGM) captured by electrodes 30 of catheter 26. Recorder 42 may include pacing capability for pacing the heart rhythm and/or may be electrically connected to a standalone pacer.

System 20 may include an ablation energy generator 48 for providing ablative energy to one or more of electrodes 30. Energy produced by ablation energy generator 48 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 50 comprises an interface for electrical communication between catheters 26, other electrophysiological equipment, a power supply, and a workstation 52 for controlling operation of system 20. Electrophysiological equipment in system 20 may include for example, multiple catheters 26, location pad 36, body surface ECG electrodes 46, electrode patches 40, ablation energy generator 48, and recorder 42. Optionally, PIU 50 additionally includes processing capability for implementing real-time computations of the position of the catheters and for processing ECG signals.

Workstation 52 includes a memory and a processor, with appropriate operating software stored in the memory, and user interface capability. Workstation 52 may provide multiple functions, optionally including (1) modeling the endocardial anatomy in three-dimensions (3D) and rendering the model or an anatomical map 54 for display on a display device 56; (2) displaying on display device 56 activation sequences (or other data) compiled from recorded electrograms 44 in representative visual indicia or imagery superimposed on the rendered anatomical map 54; (3) displaying real-time location and orientation of one or more catheters within heart 24; and (4) displaying on display device 56 sites of interest such as places where ablation energy has been applied. A commercial product embodying elements of system 20 is the CARTO® 3 System, available from Biosense Webster, Inc. (31A Technology Drive, Irvine, CA 92618).

Figure 2:
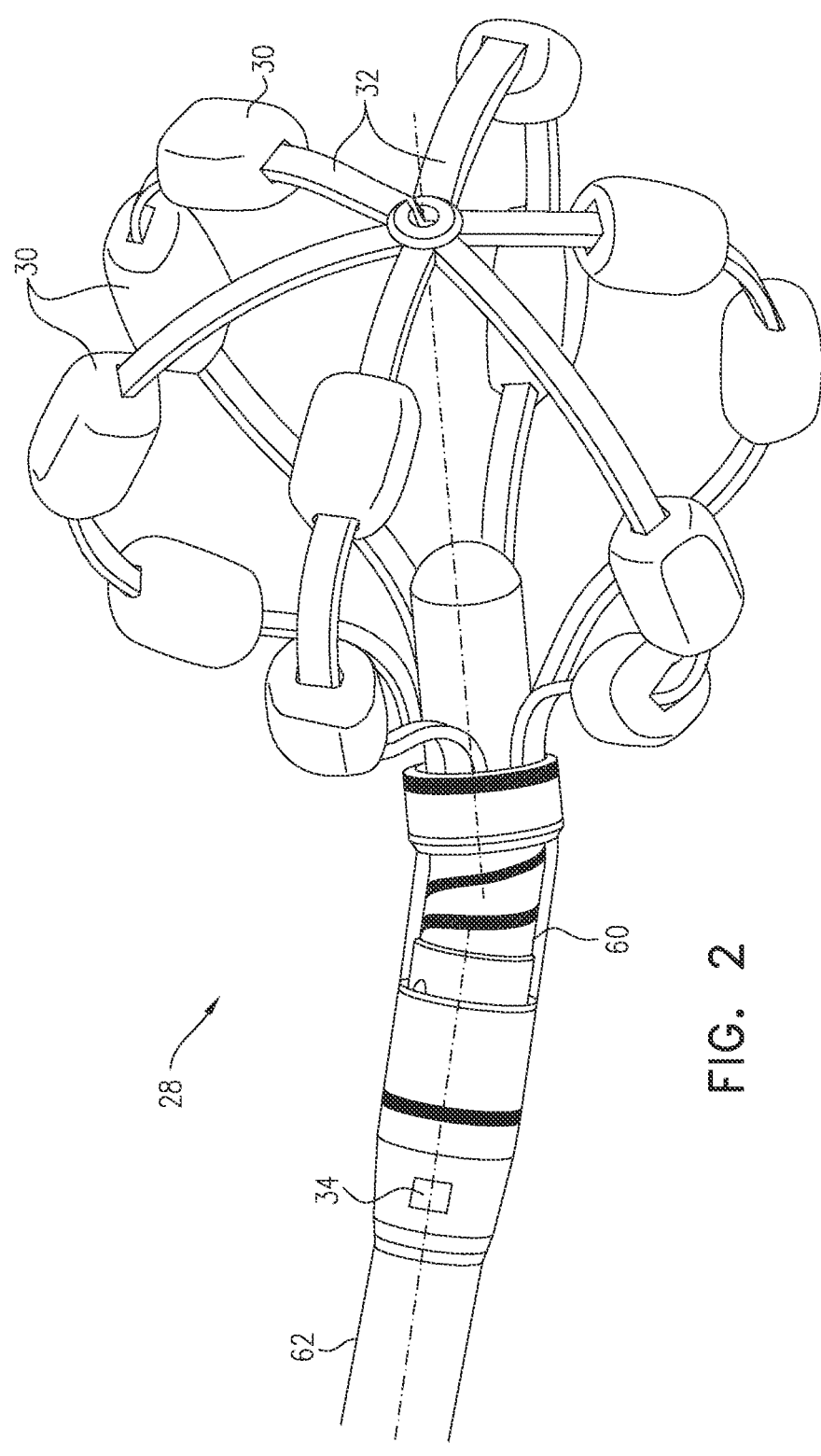
FIG. 2 is a schematic detail view showing a basket assembly at the distal end of a catheter, in accordance with an example of the present disclosure.

FIG. 2 is a schematic pictorial illustration of basket assembly 28, in accordance with an example of the disclosure. Basket assembly 28 comprises multiple resilient spines 32, with electrodes 30 disposed along the spines. Although basket assembly 28 is shown as comprising six spines 32, in alternative embodiments the basket assembly may comprise a larger or smaller number of spines.

Spines 32 typically comprise a suitable resilient metal or plastic material, for example. The proximal tips of spines 32 are joined mechanically at the proximal end of basket assembly 28, where the basket assembly connects via a joint 60 to the distal end of an insertion tube 62 of catheter 26. The distal tips of spines 32 are likewise joined together mechanically at the distal end of the basket assembly. The spines are compresses as catheter 26 is inserted through a sheath (not shown) and then bow radially outward when basket assembly 28 is deployed from the sheath into the heart chamber. The diameter of the basket assembly when deployed is typically in the range of 10-20 mm, but larger or small assemblies may alternatively be used, depending on application requirements. Once basket assembly 28 has been deployed in the heart chamber, physician 22 manipulates catheter 26 so that electrodes 30 contact myocardial tissue at target locations in the heart chamber.

Basket assembly 28 may comprise other components, as well (not shown in the figures), such as ultrasound transducers and temperature sensors. Electrodes 30, as well as these other components, are connected to wires (not shown) running through insertion tube 62 to the proximal end of catheter 26, where they connect to appropriate circuitry in PIU 50. Further details of the construction of basket assembly 28 are presented, for example, in U.S. Provisional Patent Application 63/336,094, filed Apr. 4, 2022 (BIO6693), whose disclosure is incorporated herein by reference. Alternatively, other designs of the electrodes and spines may be used, as will be apparent to those skilled in the art after reading the present description.

Joint 60 deforms in response to force exerted by basket assembly 28 against tissue within the heart chamber. For example, joint 60 may deflect in response to lateral forces as illustrated in FIG. 2, so that the central axis of basket assembly 28 is angled relative to the longitudinal axis of insertion tube 62. In some cases, the deflection angle may be as much as 30°. The degree and direction of deformation of joint 60 is indicative of the magnitude and direction of the force. The deformation is measured using magnetic transducers as described hereinbelow.

Figure 3:
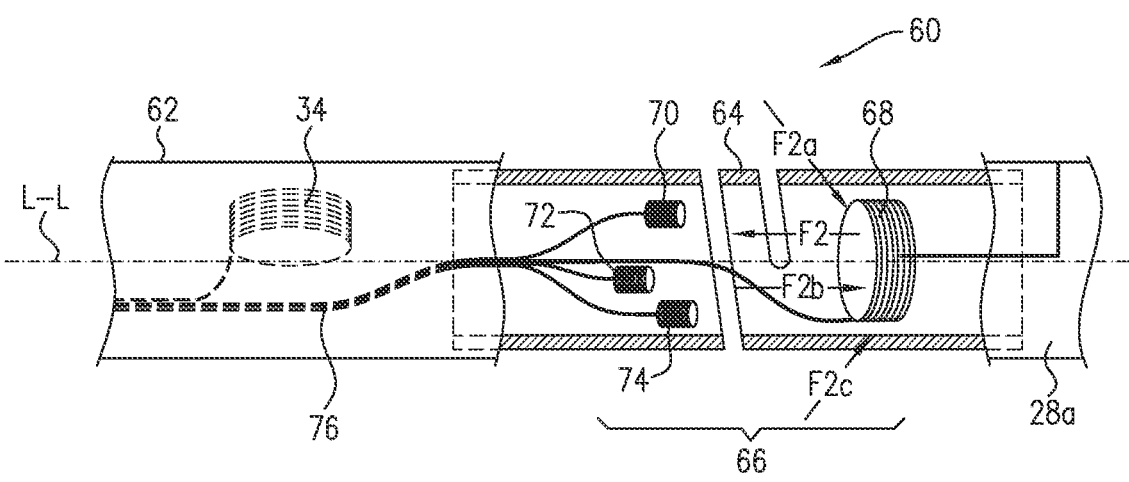
FIG. 3 is a schematic sectional view showing details of the distal part of a catheter, in accordance with an example of the present disclosure.

FIG. 3 is a schematic, sectional view of joint 60 and associated components in the distal part of catheter 26, showing details of the structure of the catheter in accordance with an example of the disclosure. Insertion tube 62 (extending along longitudinal axis L-L) is connected to a proximal portion 28a of basket assembly 28 by joint 60, as noted above. Insertion tube 62 and joint 60 are covered by a flexible, insulating material (which is cut away in FIG. 3 to expose the internal structure of the catheter).

Joint 60 comprises a resilient coupling member 64. In the pictured example, coupling member 64 has the form of a tubular piece of an elastic material, with a helical cut along a portion of its length. For example, the coupling member may comprise a superelastic alloy, such as nickel titanium (Nitinol). The helical cut causes the tubular piece to behave like a spring in response to forces exerted on basket assembly 28. Further details regarding the fabrication and characteristics of this sort of coupling member are presented, for example, in U.S. Pat. No. 8,437,832, whose disclosure is incorporated herein by reference. Details of joint 60 are also indicated as element 400 in the previously mentioned U.S. Provisional Patent Application 63/336,094, filed Apr. 4, 2022 (BIO6693). Alternatively, the coupling member may comprise a coil spring or any other suitable sort of resilient component with the desired flexibility and strength characteristics. In an alternative embodiment (not shown in the figures), the joint is an integral part of insertion tube 62, and coupling member 64 may take the form of a cut in the insertion tube itself.

The stiffness of coupling member 64 determines the range of relative movement between basket assembly 28 and insertion tube 62 in response to forces exerted on the basket assembly 28, for example due to pressure against the endocardium during an ablation procedure. Coupling member 64 is configured to permit deformation, including axial displacement (i.e., movement along the axis of insertion tube 62) and angular deflection of basket assembly 28, in proportion to the force on the basket assembly. Measurement of the displacement and deflection gives an indication of the force and thus helps to ensure that the correct force is applied during ablation.

A joint sensing assembly 66, comprising coils 68, 70, 72 and 74 within joint 60, provides accurate readings of the position of basket assembly 28 relative to the distal end of insertion tube 62, including axial displacement and angular deflection. These coils are one type of magnetic transducer that may be used in implementations of the present disclosure. Although the embodiments described herein use coils as magnetic transducers, other types of magnetic transducers may be used in alternative embodiments, as will be apparent to those skilled in the art.

The coils in joint sensing assembly 66 are divided between two subassemblies on opposite sides of coupling member 64: One subassembly, on the distal side of coupling member 64, comprises coil 68 (affixed to proximal portion 28a of basket 28), which coil 68 is driven by a current via a cable 76 from PIU 50 to generate a first AC magnetic field at a predefined frequency internal to the probe. This first AC magnetic field is received by a second subassembly on the proximal side of coupling member 64, comprising location sensing coils 70, 72 and 74, which are spaced axially apart from coil 68. (The term "axial," as used in the context of the present patent application and in the claims, refers to the direction of the longitudinal axis L-L of the distal part of insertion tube 62.) Coils 70, 72 and 74 emit electrical signals at the predefined frequency in response to the first AC magnetic field generated by coil 68 disposed in the probe 60. These signals are conveyed by cable 76 to PIU 50, which processes the signals in order to measure the axial displacement and angular deflection of joint 60 and thus to calculate both the disposition (i.e., displacement and angulation relative to the L-L axis) of basket assembly 28 and the force exerted by the basket assembly against the tissue.

Various other configurations of the coils in the sensing subassemblies may also be used, as alternatives to the configuration shown and described above. For example, the positions of the subassemblies may be reversed, so that that the field generating coil is on the proximal side of joint 64, and the sensor coils are on the distal side. As another alternative, coils 70, 72 and 74 may be driven as field generators (using time- and/or frequency-multiplexing to distinguish the fields), while coil 68 also serves as the magnetic field sensor. The sizes and numbers of the coils in FIG. 3 are shown only by way of example, and larger or smaller numbers of coils may similarly be used, in various different positions, so long as one of the subassemblies comprises at least two coils in different radial positions, to allow differential measurement of joint deflection.

At least one of coils 68, 70, 72 and 74 is also used to output signals in response to the AC magnetic fields generated by field generators 38 (FIG. 1), and thus serves as a position sensing coil. Preferably, coil 68 is utilized for this purpose. Position sensor 34, in the distal end of insertion tube 62 proximal to joint 60, also generates signals in response to the second AC magnetic fields of field generators 38 (FIG. 1). (The frequencies of the second AC magnetic fields produced by field generators 38 are different from that of the first AC magnetic field generated by coil 68, but could be in the same multi-kilohertz range.) Each AC magnetic field generator 38a, 38b, 38c provides respective and distinct AC magnetic fields in order for PIU 50 to triangulate the three distinct time varying second magnetic fields so as to arrive at a location in space. In the preferred embodiments, each coil (from coils 38a, 38b, 38c) may have three coils oriented in X, Y and Z planes so that the magnetic field generators external to the patient may have a total of nine (9) magnetic field coils and hence nine (9) different time-varying magnetic fields (e.g., frequencies) for location determination by the internal coils in the catheter. PIU 50 processes these signals in order to calculate position coordinates (location and orientation) both of position sensor 34 and of one or more of coils 68, 70, 72 and 74, and combines the results of these calculations to find the location and orientation coordinates of basket assembly 28 in three dimensions in the external frame of reference that is defined by location pad 36.

Figure 4:
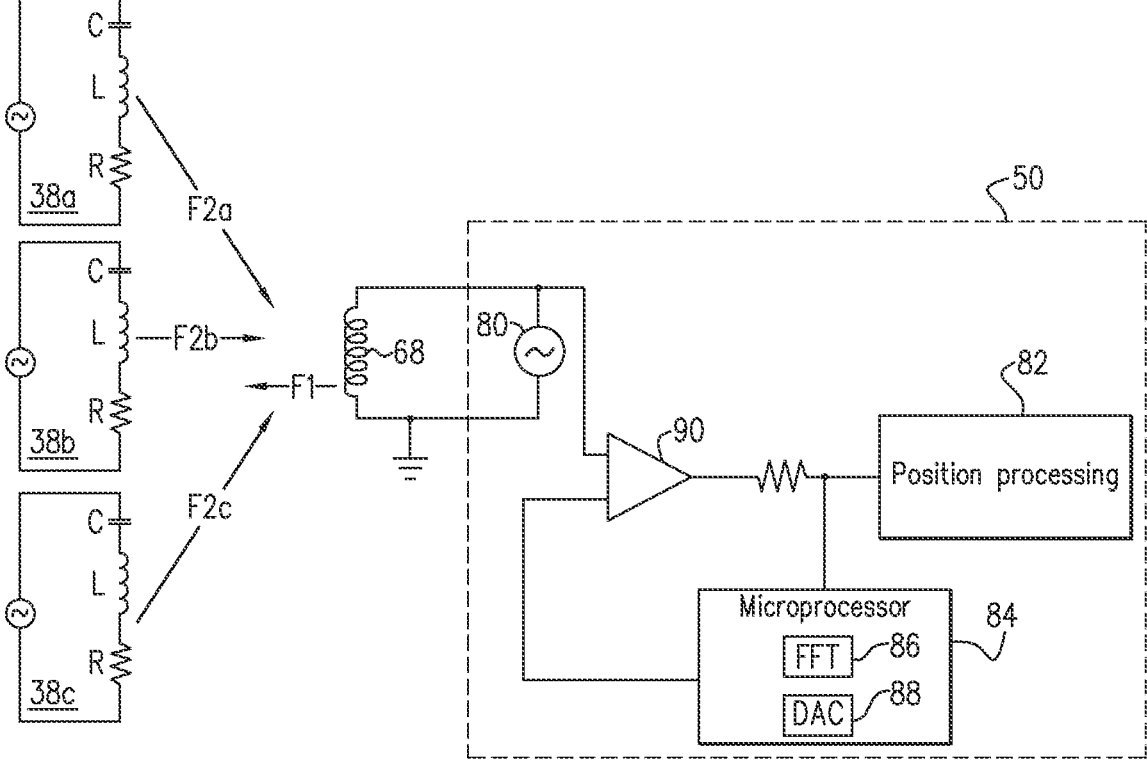
FIG. 4 is a block diagram that schematically illustrates sensing and signal processing circuits associated with a catheter, in accordance with an example of the disclosure.

FIG. 4 is a block diagram that schematically illustrates sensing and signal processing circuits used in finding position coordinates of basket assembly 28, based on the position signal output by coil 68 in response to the second AC magnetic fields produced by external AC magnetic field generators 38a, 38b, 38c (also shown in FIG. 1), in accordance with an example of the disclosure. During this position-finding process, a signal generator 80 drives coil 68 to generate its own magnetic field, i.e., first AC magnetic field F1, which is used by joint sensing assembly 66 in measuring the force on joint 60. The driving signal applied to coil 68 by signal generator 80 at the frequency of the force sensor (referred to hereinafter as the "first frequency" for the first AC magnetic field) is far stronger than the position signal output by coil 68 at the frequency of external or second AC magnetic field generators 38 (the "second frequency") F2a, F2b, or F2c. To enable calculation of the position coordinates of basket assembly 28, the control circuitry in PIU 50 cancels interference at the first frequency of the first AC magnetic field F1 from the signal output by coil 68. Position processing circuitry 82 can then process the remaining signal component at the second frequency F2a-F2c of the second AC magnetic fields (from magnetic field generators 38a, 38b and 38c) in order to calculate the position coordinates accurately. It should be noted for precision that each magnet field generator 38a-38c may generate more than one frequency, e.g., F2aX, F2aY, F2aZ for generator 38a, F2bX, F2bY, F2bZ for generator 38b and frequencies F2CX, F2cY, and F2cZ for generator 38c, where "X", "Y" and "Z" indicate the intended axes for each frequency F2a, F2b, F2c.

To enable effective cancellation of the interference at the first frequency, a microprocessor 84 measures the amplitude of the interference at the first frequency that is present in the signal received by PIU 50 from coil 68. Microprocessor 84 generates an interference cancellation signal having this same measured amplitude at the first frequency and subtracts the interference cancellation signal from the signal received by PIU 50 from coil 68. This signal subtraction or cancellation is preferable to simply filtering the signal received by PIU 50 from coil 68 because the interference at the first frequency is much stronger than the signal component at the second frequency.

In the specific example that is shown in FIG. 4, microprocessor 84 digitizes the signal received by PIU 50 from coil 68 and transforms the digitized signal to the frequency domain, for example using a Fast Fourier Transform (FFT) 86. Microprocessor 84 extracts the amplitude and a phase of the component of the signal at the first frequency, and generates the interference cancellation signal as a digital signal at the same, measured amplitude, but in antiphase to the measured signal component at the first frequency. A digital/analog converter (DAC) 88 converts the digital signal to an analog interference cancellation signal. The analog interference cancellation signal is subtracted from the signal received by PIU 50 from coil 68 by inputting both signals together to an analog adder 90.

Although the present example relates specifically to a configuration in which coil 68, on the distal side of joint 60, both generates a magnetic field (the first AC magnetic field) and senses the second AC magnetic fields of respective magnetic field generators 38a, 38b, and 38c of location pad 36, the principles of this example may alternatively be applied in other configurations. For example, similar techniques for interference cancellation may be applied when the magnetic field of joint sensor 66 is generated by one or more of coils 70, 72, and 74 and sensed by coil 68. All such alternative configurations are within the scope of the present disclosure.

Method for Position Sensing

FIG. 5 is a flow chart that schematically illustrates a method for position sensing, in accordance with an example of the disclosure. The method is initiated by providing a probe having a distal part adapted for insertion into a body of a living subject, at a probe provision step 100. The probe comprises first and second magnetic transducers disposed at respective first and second locations in the distal part of the probe. At least one external magnetic field generator is placed external to the probe, at a field generator placement step 102.

The first magnetic transducer is driven to generate a first AC magnetic field at a first frequency, at a first transducer driving step 104. The at least one external magnetic field generator is driven to generate a second AC magnetic field at a second frequency, at a second transducer driving step 106. A disposition of the distal part of the probe is calculated by processing a first signal output by the second magnetic transducer at the first frequency, at a disposition calculation step 108. Position coordinates of the distal part of the probe are calculated by processing a component of a second signal output by one of the first and second magnetic transducers at the second frequency while canceling from the second signal interference at the first frequency, at a coordinate calculation step 110.

Examples

Example 1. Medical apparatus (20) comprises a probe (26) comprising a distal part (28) adapted for insertion into a body of a living subject (23) and comprising first and second magnetic transducers (68, 70, 72, 74) disposed at respective first and second locations in the distal part of the probe. A magnetic field generator (38) is disposed apart from the probe and adapted for placement in proximity to the body of the living subject. Control circuitry (50) is configured to drive the first magnetic transducer to generate a first AC magnetic field at a first frequency and to drive the magnetic field generator to generate a second AC magnetic field at a second frequency, to calculate a disposition of the distal part of the probe by processing a first signal output by the second magnetic transducer at the first frequency, and to calculate position coordinates of the distal part of the probe by processing a component of a second signal output by one of the first and second magnetic transducers at the second frequency while canceling from the second signal interference at the first frequency.

Example 2. The apparatus according to example 1, wherein the first and second magnetic transducers respectively comprise first and second coils, and the control circuitry is configured to drive the first magnetic transducer by applying an AC electrical current at the first frequency to the first coil.

Example 3. The apparatus according to example 1 or 2, wherein the distal part of the probe comprises a joint, which is configured to deform in response to a force exerted by the distal part of the probe against tissue, and wherein the first and second magnetic transducers are disposed on opposing sides of the joint.

Example 4. The apparatus according to example 3, wherein the control circuitry is configured to calculate a deformation of the joint responsively to the first signal output by the second magnetic transducer at the first frequency, and to measure the force exerted by the distal part of the probe against the tissue based on the calculated deformation.

Example 5. The apparatus according to example 3 or 4, wherein the first magnetic transducer is disposed on a distal side of the joint, while the second magnetic transducer is disposed on a proximal side of the joint.

Example 6. The apparatus according to any of examples 3-5, wherein the probe comprises a third magnetic transducer in a third location, proximal to the first and second locations, and wherein the control circuitry is configured to calculate the position coordinates of the distal part of the probe by both processing the second signal and processing a third signal output by the third magnetic transducers at the second frequency.

Example 7. The apparatus according to any of the preceding examples, wherein the distal part of the probe comprises a basket assembly, comprising multiple spines and electrodes, which are disposed along the spines and configured to contact tissue.

Example 8. The apparatus according to any of the preceding examples, wherein the control circuitry is configured to cancel the interference by measuring an amplitude of the interference in the second signal at the first frequency, generating a third signal having the measured amplitude at the first frequency, and subtracting the third signal from the second signal.

Example 9. The apparatus according to example 8, wherein the control circuitry is configured to measure the amplitude of the interference by digitizing the second signal and extracting the amplitude and a phase of an element of the digitized second signal at the first frequency, and to generate the third signal as a digital signal at the measured amplitude in antiphase to the element of the digitized second signal at the first frequency and convert the digital signal to an analog interference cancellation signal, and to subtract the third signal from the second signal by analog summation of the analog interference cancellation signal with the second signal.

Example 10. The apparatus according to example 9, wherein the second signal is output by the first magnetic transducer while the first magnetic transducer is driven to generate the first AC magnetic field.

Example 11. A method for position sensing comprises providing a probe (26) having a distal part (28) adapted for insertion into a body of a living subject (23) and comprising first and second magnetic transducers (68, 70, 72, 74) disposed at respective first and second locations in the distal part of the probe. A magnetic field generator (38) is placed in proximity to the body. The first magnetic transducer to is driven to generate a first AC magnetic field at a first frequency while the probe is inside the body. The magnetic field generator is driven to generate a second AC magnetic field at a second frequency. A disposition of the distal part of the probe is calculated by processing a first signal output by the second magnetic transducer at the first frequency. Position coordinates of the distal part of the probe are calculated by processing a component of a second signal output by one of the first and second magnetic transducers at the second frequency while canceling from the second signal interference at the first frequency.

The implementations described above are cited by way of example, and the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. Medical apparatus, comprising:
   a probe comprising a distal part adapted for insertion into a body of a living subject and comprising first and second magnetic transducers disposed at respective first and second locations in the distal part of the probe;
   at least one magnetic field generator disposed externally to the probe and adapted for placement in proximity to the body of the living subject; and
   control circuitry configured to
   (a) drive the first magnetic transducer in the probe to generate a first alternating-current (AC) magnetic field at a first frequency,
   (b) drive the at least one magnetic field generator external to the probe to generate a second AC magnetic field at a second frequency,
   (c) calculate a disposition of the distal part of the probe by processing a first signal output by the second magnetic transducer at the first frequency of the first AC magnetic field generated by the first magnetic transducer, and
   (d) calculate position coordinates of the distal part of the probe by processing a component of a second signal output by one of the first and second magnetic transducers at the second frequency of the second AC magnetic field generated by the magnetic field generator external to the probe while canceling from the second signal interference at the first frequency of the first AC magnetic field generated by the first magnetic transducer.

2. The apparatus according to claim 1, wherein the first and second magnetic transducers respectively comprise first and second coils, and the control circuitry is configured to drive the first magnetic transducer by applying an AC electrical current at the first frequency to the first coil.

3. The apparatus according to claim 1, wherein the distal part of the probe comprises a joint, which is configured to deform in response to a force exerted by the distal part of the probe against tissue, and wherein the first and second magnetic transducers are disposed on opposing sides of the joint.

4. The apparatus according to claim 3, wherein the control circuitry is configured to calculate a deformation of the joint responsively to the first signal output by the second magnetic transducer at the first frequency of the first AC magnetic field generated by the first magnetic transducer, and to measure the force exerted by the distal part of the probe against the tissue based on the calculated deformation.

5. The apparatus according to claim 3, wherein the first magnetic transducer is disposed on a distal side of the joint, while the second magnetic transducer is disposed on a proximal side of the joint.

6. The apparatus according to claim 3, wherein the probe comprises a third magnetic transducer in a third location, proximal to the first and second locations, and wherein the control circuitry is configured to calculate the position coordinates of the distal part of the probe by both processing the second signal and processing a third signal output by the third magnetic transducer at the second frequency of the second AC magnetic field generated by the magnetic field generator external to the probe.

7. The apparatus according to claim 1, wherein the distal part of the probe comprises a basket assembly, the basket assembly comprising multiple spines and electrodes, the electrodes disposed along the spines and configured to contact tissue within a cavity in the body.

8. The apparatus according to claim 1, wherein the control circuitry is configured to cancel the interference by measuring an amplitude of the interference in the second signal at the first frequency of the first AC magnetic field generated by the first magnetic transducer, generating a third signal having the measured amplitude at the first frequency of the first AC magnetic field generated by the first magnetic transducer, and subtracting the third signal from the second signal.

9. The apparatus according to claim 8, wherein the control circuitry is configured to measure the amplitude of the interference by digitizing the second signal and extracting the amplitude and a phase of an element of the digitized second signal at the first frequency of the first AC magnetic field generated by the first magnetic transducer, and to generate the third signal as a digital signal at the measured amplitude in antiphase to the element of the digitized second signal at the first frequency of the first AC magnetic field generated by the first magnetic transducer and convert the digital signal to an analog interference cancellation signal, and to subtract the third signal from the second signal by analog summation of the analog interference cancellation signal with the second signal.

10. The apparatus according to claim 9, wherein the second signal is output by the first magnetic transducer while the first magnetic transducer is driven to generate the first AC magnetic field.

11. A method for position sensing, comprising:

providing a probe having a distal part adapted for insertion into a body of a living subject and comprising first and second magnetic transducers disposed at respective first and second locations in the distal part of the probe;

placing at least one external magnetic field generator external to the probe;

driving the first magnetic transducer to generate a first AC magnetic field at a first frequency;

driving the at least one external magnetic field generator to generate a second AC magnetic field at a second frequency;

calculating a disposition of the distal part of the probe by processing a first signal output by the second magnetic transducer at the first frequency of the first AC magnetic field generated by the first magnetic transducer; and calculating position coordinates of the distal part of the probe by processing a component of a second signal output by one of the first and second magnetic transducers at the second frequency of the second AC magnetic field generated by the magnetic field generator external to the probe while canceling from the second signal interference at the first frequency of the first AC magnetic field generated by the first magnetic transducer.

12. The method according to claim 11, wherein the first and second magnetic transducers respectively comprise first and second coils, and driving the first magnetic transducer comprising applying an AC electrical current at the first frequency to the first coil.

13. The method according to claim 11, wherein the distal part of the probe comprises a joint, which is configured to deform in response to a force exerted by the distal part of the probe against tissue, and wherein the first and second magnetic transducers are disposed on opposing sides of the joint.

14. The method according to claim 13, wherein calculating the disposition of the distal part of the probe comprises calculating a deformation of the joint responsively to the first signal output by the second magnetic transducer at the first frequency of the first AC magnetic field generated by the first magnetic transducer, and measuring the force exerted by the distal part of the probe against the tissue based on the calculated deformation.

15. The method according to claim 13, wherein the first magnetic transducer is disposed on a distal side of the joint, while the second magnetic transducer is disposed on a proximal side of the joint.

16. The method according to claim 13, wherein the probe comprises a third magnetic transducer in a third location, proximal to the first and second locations, and wherein calculating the position coordinates comprises finding the position coordinates of the distal part of the probe by both processing the second signal and processing a third signal output by the third magnetic transducer at the second frequency of the second AC magnetic field generated by the magnetic field generator external to the probe.

17. The method according to claim 11, wherein the distal part of the probe comprises a basket assembly, the basket assembly comprising multiple spines and electrodes, the electrodes are disposed along the spines and configured to contact tissue.

18. The method according to claim 11, wherein canceling the interference comprises measuring an amplitude of the interference in the second signal at the first frequency of the first AC magnetic field generated by the first magnetic transducer, generating a third signal having the measured amplitude at the first frequency of the first AC magnetic field generated by the first magnetic transducer, and subtracting the third signal from the second signal.

19. The method according to claim 18, wherein measuring the amplitude of the interference comprises digitizing the second signal and extracting the amplitude and a phase of an element of the digitized second signal at the first frequency of the first AC magnetic field generated by the first magnetic transducer, and wherein generating the third signal comprises generating a digital signal at the measured amplitude in antiphase to the element of the digitized second signal at the first frequency of the first AC magnetic field generated by the first magnetic transducer and converting the digital signal to an analog interference cancellation signal, and wherein subtracting the third signal from the second signal comprises performing an analog summation of the analog interference cancellation signal with the second signal.

20. The method according to claim 19, wherein the second signal is output by the first magnetic transducer while the first magnetic transducer is driven to generate the first AC magnetic field.

\* \* \* \* \*